(12) United States Patent
Kroecker et al.

(10) Patent No.: US 7,970,450 B2
(45) Date of Patent: Jun. 28, 2011

(54) WIRELESS MEDICAL MONITORING APPARATUS AND SYSTEM

(75) Inventors: Stephan V. Kroecker, Titusville, FL (US); Richard L Krampe, Casselberry, FL (US); Michael Vosch, Titusville, FL (US)

(73) Assignee: Halthion Medical Technologies, Inc., Tampa, FL (US)

( * ) Notice: Subject to any disclaimer, the term of this patent is extended or adjusted under 35 U.S.C. 154(b) by 405 days.

(21) Appl. No.: 10/476,437

(22) PCT Filed: May 3, 2002

(86) PCT No.: PCT/US02/13966
§ 371 (c)(1),
(2), (4) Date: Oct. 30, 2003

(87) PCT Pub. No.: WO02/089667
PCT Pub. Date: Nov. 14, 2002

(65) Prior Publication Data
US 2006/0155183 A1    Jul. 13, 2006

Related U.S. Application Data

(60) Provisional application No. 60/288,587, filed on May 3, 2001.

(51) Int. Cl.
*A61B 5/0402* (2006.01)
(52) U.S. Cl. .................. 600/391; 600/393; 600/509
(58) Field of Classification Search .......... 600/391–393, 600/509; 128/903
See application file for complete search history.

(56) References Cited

U.S. PATENT DOCUMENTS

| | | | | |
|---|---|---|---|---|
| 3,943,918 A * | 3/1976 | Lewis | ................. | 600/392 |
| 4,121,573 A * | 10/1978 | Crovella et al. | ................. | 600/391 |
| 5,042,481 A * | 8/1991 | Suzuki et al. | ................. | 600/393 |
| 5,168,874 A * | 12/1992 | Segalowitz | ................. | 600/393 |
| 5,224,479 A * | 7/1993 | Sekine | ................. | 600/393 |
| 5,634,468 A * | 6/1997 | Platt et al. | ................. | 600/509 |
| 6,035,230 A * | 3/2000 | Kang et al. | ................. | 600/509 |
| 6,285,899 B1 * | 9/2001 | Ghaem et al. | ................. | 600/391 |
| 6,289,238 B1 * | 9/2001 | Besson et al. | ................. | 600/509 |
| 6,315,719 B1 * | 11/2001 | Rode et al. | ................. | 600/391 |
| 6,363,274 B1 * | 3/2002 | Scalisi et al. | ................. | 600/523 |
| 6,385,473 B1 * | 5/2002 | Haines et al. | ................. | 600/393 |
| 6,400,975 B1 * | 6/2002 | McFee | ................. | 600/372 |
| 6,450,953 B1 * | 9/2002 | Place et al. | ................. | 600/300 |
| 6,494,829 B1 * | 12/2002 | New et al. | ................. | 600/300 |
| 6,569,094 B2 * | 5/2003 | Suzuki et al. | ................. | 128/903 |
| 6,694,177 B2 * | 2/2004 | Eggers et al. | ................. | 600/509 |

* cited by examiner

*Primary Examiner* — Lee S Cohen
(74) *Attorney, Agent, or Firm* — L. Drayer

(57) ABSTRACT

An apparatus for monitoring an electrical signal from a patient's body includes a disposable electrode patch having a thin flexible housing with an adhesive exterior, a power source, a printed circuit board, a plurality of electrodes, a converter for converting a detected electrical signal from the patient's body to a digital signal, a processor for processing the digital signal, and a transmitter connected for transmitting the processed digital signal as a wireless signal. A monitoring unit communicating with the electrode patch includes a power source, a transceiver, a global positioning receiver, a processor, at least one communication port for external communications, and a display. A system of the invention includes a plurality of patients having medical monitors wirelessly communicating biometric information to a central processor for archiving and accessing.

12 Claims, 7 Drawing Sheets

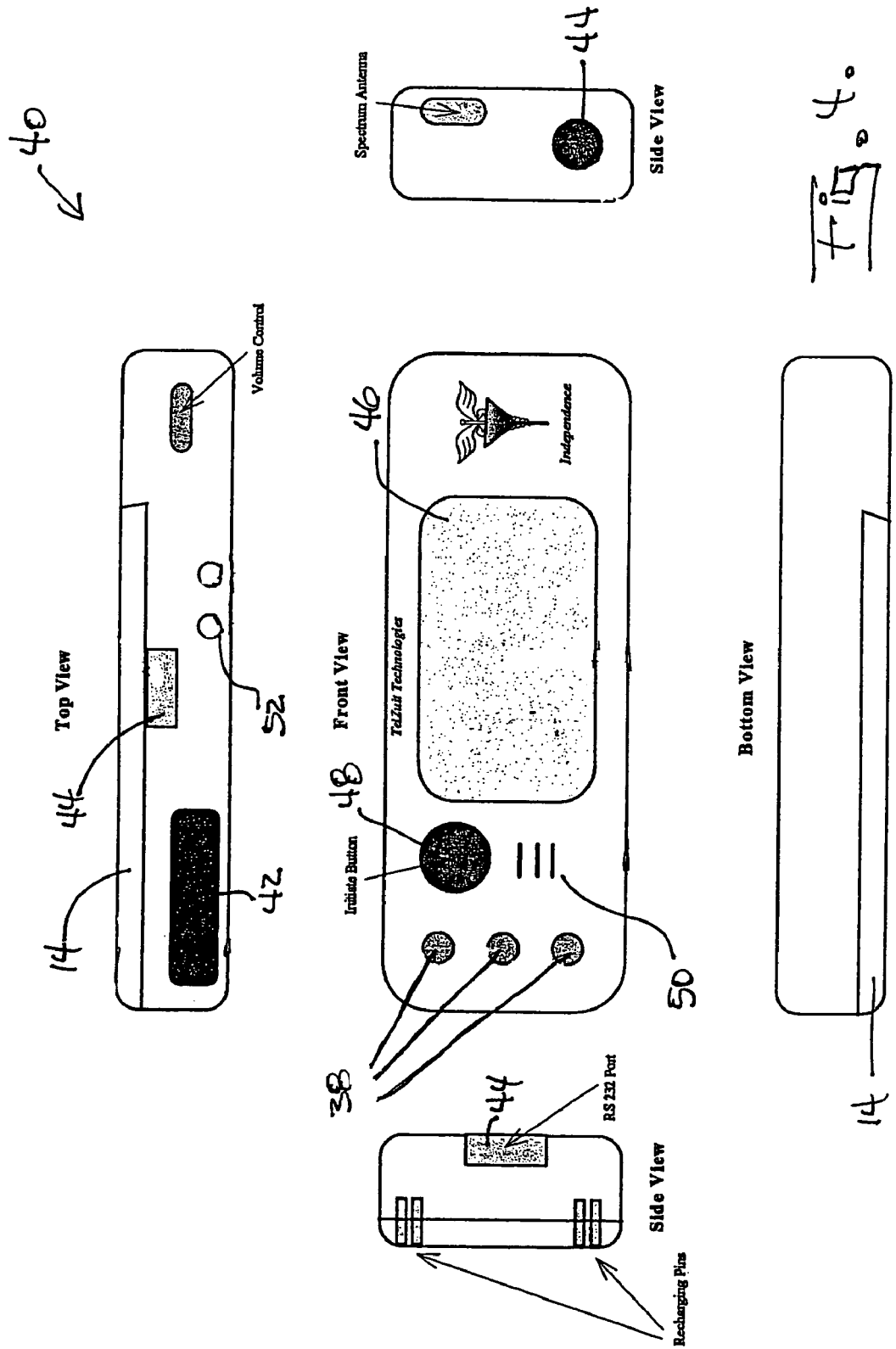

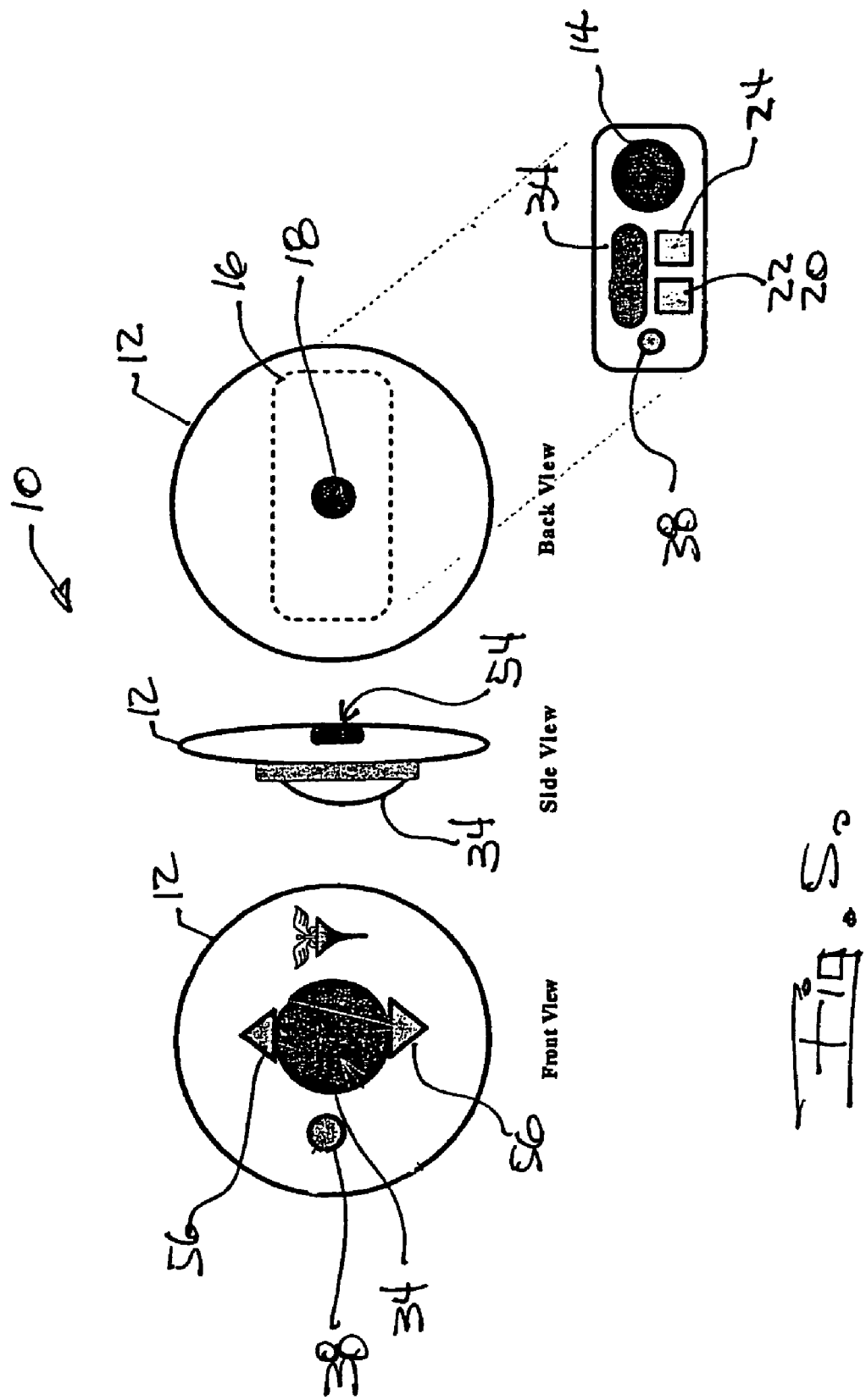

WIRELESS MEDICAL MONITORING APPARATUS AND SYSTEM

RELATED APPLICATION

This application is a 35 U.S.C. 371 filing of PCT/US02/13966, filed May 3, 2002, which claims priority from U.S. provisional application Ser. No. 60/288,587, which was flied on May 3, 2001.

FIELD OF THE INVENTION

The present invention relates to the field of medical monitoring of patients and, more particularly, to a disposable electrode patch and apparatus for wireless monitoring of medical patients.

BACKGROUND OF THE INVENTION

Monitoring of the electrical impulses generated by various organs is well known in medicine. For example, electrocardiograms, electro-encephalograms, and other similar patient monitoring methods continue to be important elements in the medical armamentarium for combating disease.

Standard methods for such medical monitoring include the attachment of electrodes to the patient's body adjacent the organ to be monitored. These electrodes are generally connected by wires to an apparatus for recording any detected electrical signals and for displaying those signals in visually perceptible form, such as in a strip chart or in on a display screen. It is easy to appreciate the limitations imposed by the requirement that the electrodes be connected to the apparatus by wires. Patient mobility is severely limited, and the tests must generally be performed in a medical office or similar setting.

To avoid some of these inconveniences, monitoring apparatuses have been developed wherein the patient wears the electrodes connected by wire to a portable recording device which the patient carries usually on a harness, a belt, or some other support. The recording device must be returned to the medical office for downloading and/or reading of the recorded data.

The aforementioned systems are unsuitable for monitoring multiple patients in real time. These prior systems are also not easily adaptable to manual activation by a patient in response to a medical event which should be recorded. Additionally, the old systems are necessarily dependent on cumbersome equipment not easily used directly by the patient.

SUMMARY OF THE INVENTION

With the foregoing in mind, the present invention advantageously provides a disposable electrode patch for monitoring of at least one electrical signal from a patient's body. The disposable patch comprises a flexible housing, a power source, electrically connected components including one or more electrodes, a signal converter, a processor, and a transmitter. The relatively thin and flexible sealed housing has an adhesive surface effective for releasably adhering the patch to the patient. The power source is positioned in the housing for providing power. A printed circuit board is positioned in the housing connected to the power source for thereby distributing power. At least one electrode is adjacent a surface of the housing and connected through the circuit board so as to detect the electrical signal when the patch is properly adhered to the patient's body. A converter is positioned in the housing connected through the circuit board to the at least one electrode for converting a detected electrical signal from the patient's body to a digital signal. The processor has a clock and is positioned in the housing connected through the circuit board to the converter for processing the digital signal responsive to time. A transmitter having a relatively flexible antenna is positioned in the housing connected to the processor through the circuit board for transmitting the processed digital signal as a wireless signal.

One preferred embodiment of the invention includes a monitoring unit comprising a power source, a transceiver in wireless communication with the disposable electrode patch, a global positioning receiver, a processor programmed at least to control the apparatus and to process signals received, at least one communication port for external communications, and a display connected to the processor to visually display information from signals processed thereby. The patient wears this monitoring unit, so that the patient's location may be tracked through the global positioning information provided by the monitoring unit.

The invention also includes a patient kit for use by a patient requiring medical monitoring. The patient kit comprises a carrying case disposed with interior cushioning material having a plurality of cavities therein for containing kit components. The various kit components are partly as described above, for example, a packet containing a plurality of disposable electrode patches, a monitoring unit, a charger for the rechargeable power source, and an instructional video recording containing instructions for the patient on proper use of kit components.

Further, the system of the invention may additionally be expanded to includea plurality of patients each individual patient of the plurality wearing a disposable electrode patch and a monitoring unit as described. A base station processor for monitoring the plurality of patients comprises a transceiver in wireless communication with each individual monitoring unit worn by the plurality of patients so as to receive therefrom signals processed thereby, and a display for displaying information contained in the received signals, including patient location information received from the global positioning system receiver.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 4 shows front, side, top and bottom elevation views of the monitoring unit used in conjunction with the patch of FIG. 1.

FIG. 5 depicts an alternate embodiment of the disposable electrode patch of the present invention, wherein the patch releasably connects to an existing electrode.

DETAILED DESCRIPTION OF THE PREFERRED EMBODIMENTS

Figure 1:
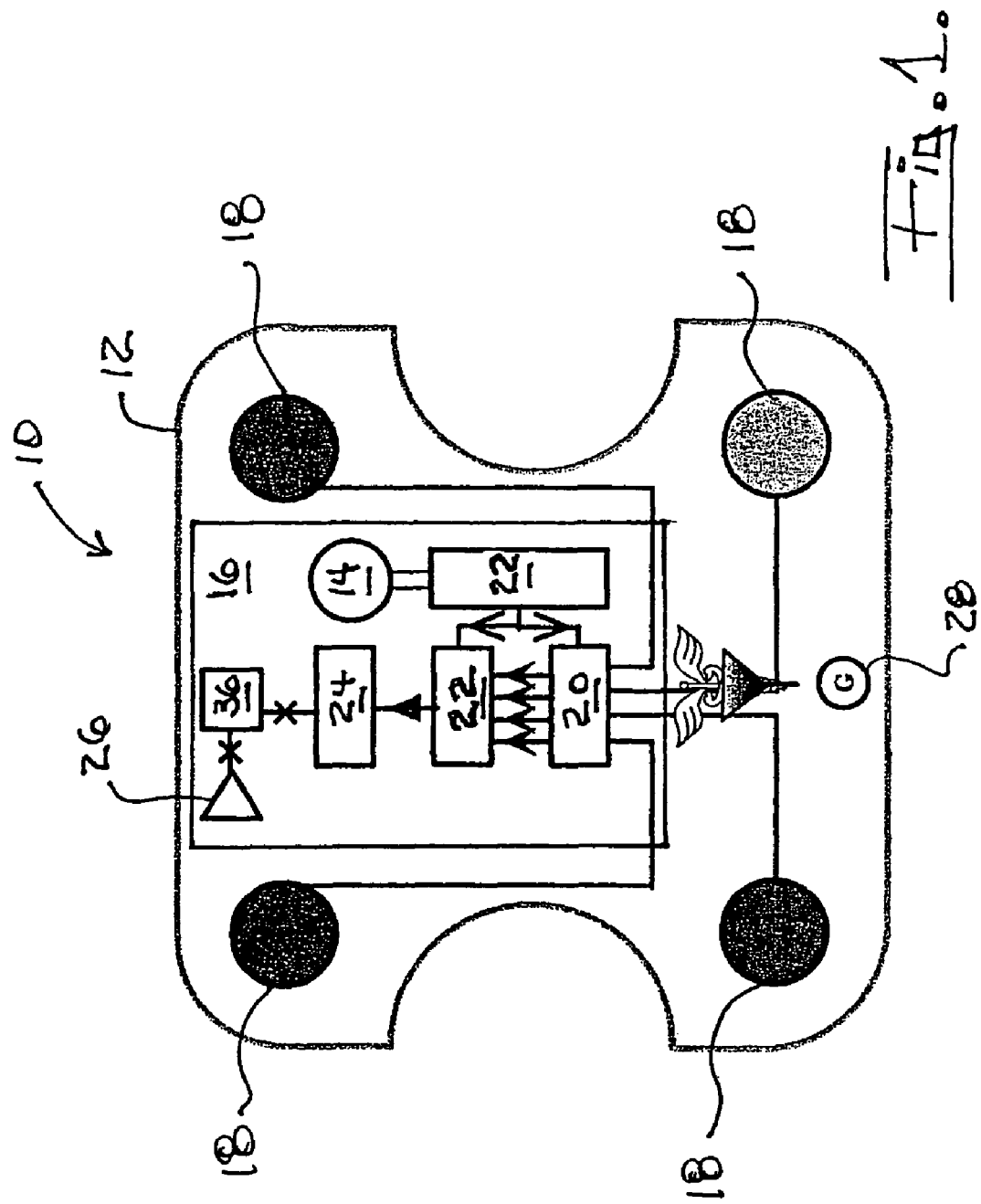
FIG. 1 is a top plan schematic of a typical disposable electrode patch according to an embodiment of the present invention.

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Accordingly, FIGS. 1 through 6 illustrate the various aspects of the present invention.

A preferred embodiment of the invention includes a disposable electrode patch 10 for monitoring of at least one electrical signal from a patient's body. The disposable electrode patch 10 comprises several elements: a relatively thin and flexible sealed housing 12 having an adhesive surface effective for releasably adhering the patch to the patient; a power source 14 positioned in the housing for providing power; a printed circuit board 16 positioned in the housing connected to the power source for thereby distributing power; at least one electrode 18 adjacent a surface of the housing and connected through the circuit board 16 so as to detect the electrical signal when the patch 10 is properly adhered to the patient's body; a converter 20 positioned in the housing connected through the circuit board 16 to the at least one electrode 18 for converting a detected electrical signal from the patient's body to a digital signal; a processor 22 having a clock and positioned in the housing connected through the circuit board 16 to the converter 20 for processing the digital signal responsive to time; and a transmitter 24 having a relatively flexible antenna 26 and positioned in the housing connected to the processor 22 through the circuit board 16 for transmitting the processed digital signal as a wireless signal.

Figure 2:
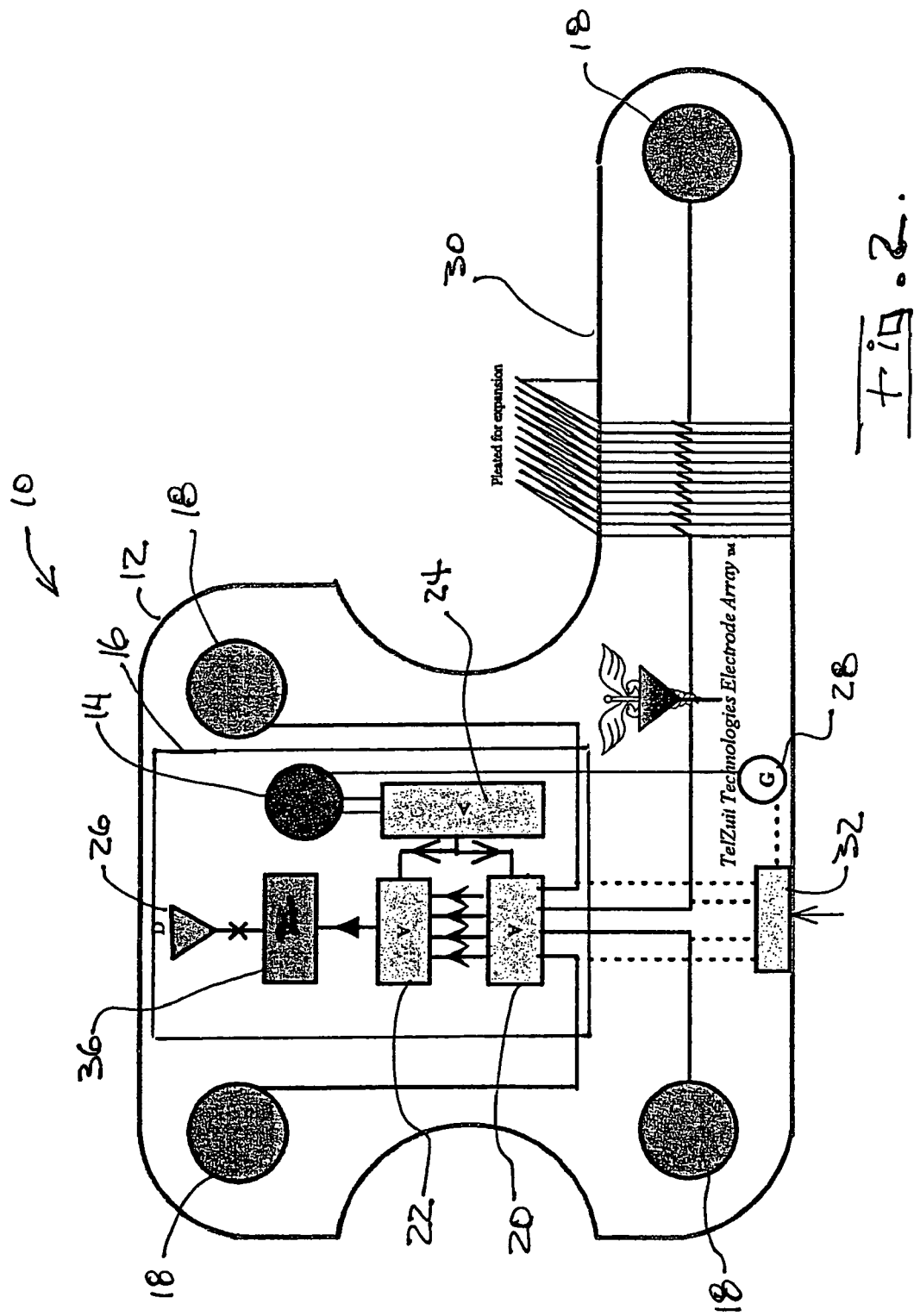
FIG. 2 shows an alternate embodiment of the disposable patch of FIG. 1, wherein the patch includes an adjustably extendable housing member.
Figure 3:
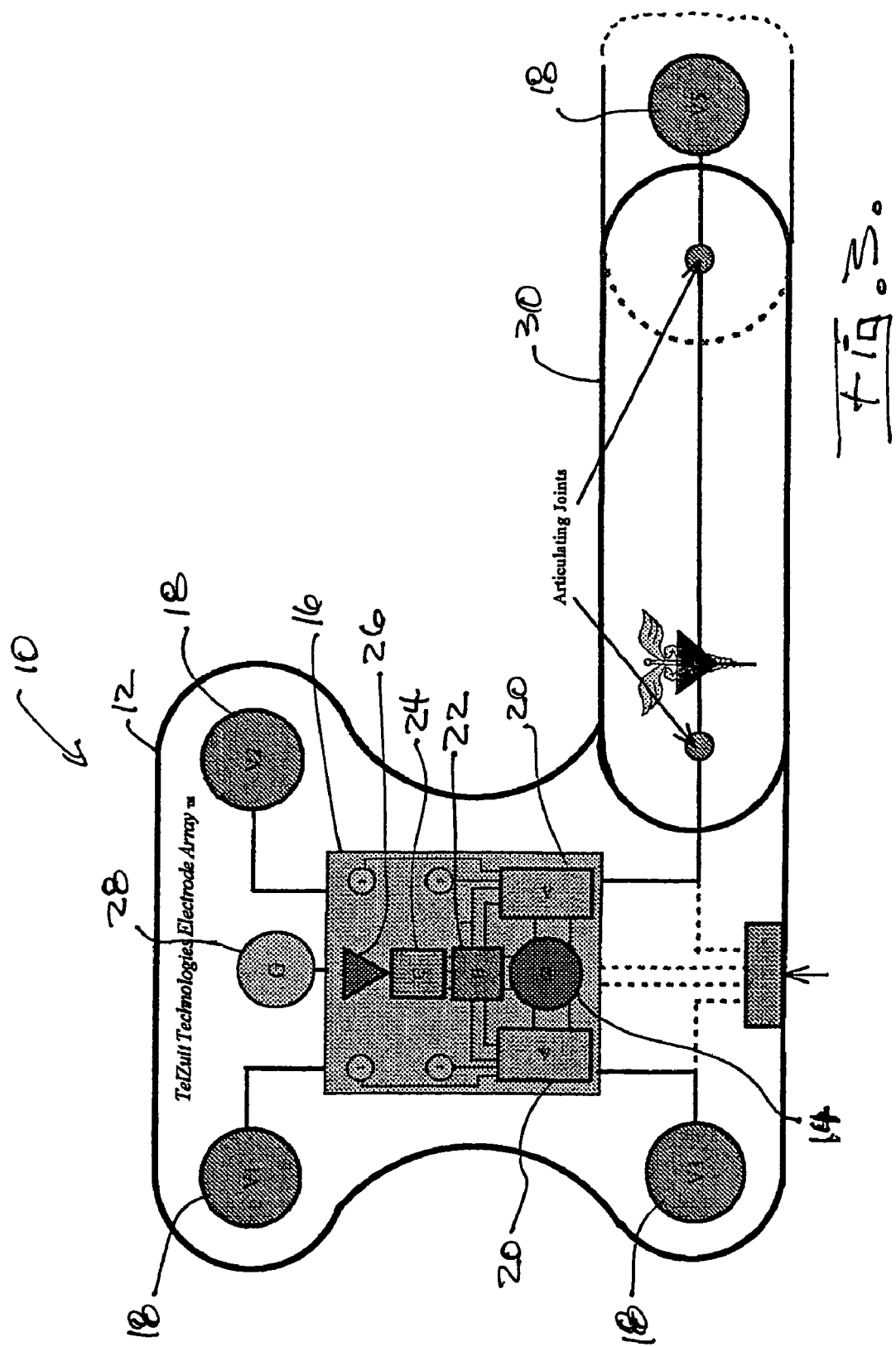
FIG. 3 shows an alternate embodiment of the disposable patch of FIG. 1, wherein the patch has an extendable housing member pivotably connected to the housing.

Preferably, as shown in FIG. 1, the electrode patch 10 may further comprise a plurality of electrodes 18 having a sufficient number of individual electrodes for effectively detecting a cardiac electrical signal. The disposable electrode patch 10 may also include other preferable features, such as a ground electrode 28 for grounding the electrode patch to the patient's body. The patch 10 may include a plurality of electrodes wherein at least one individual electrode 18 of the plurality of electrodes is positioned on a housing member 30 extending outwardly from the housing so as to allow predetermined placement on the patient's body of the individual electrode spaced apart relative to the housing, as seen in FIGS. 2 and 3. In these embodiments, the housing member 30 is adjustably extendable from the housing (FIG. 2), or pivotably connected to the housing (FIG. 3). The electrode patch 10 preferably also includes a hardwire connector 32 for transmitting the processed digital signal by wire as a backup to wireless, as seen in FIGS. 2 and 3.

In additional aspects of the invention, the housing 12 is advantageously constructed from a plurality of laminated layers comprising woven material and plastic. As known to those skilled in the art, the electrode patch 10 includes electrodes having an electrically conductive gel. The circuit board 16 optionally comprises an activation switch 34 allowing a patient to manually activate the electrode patch 10.

In another preferred embodiment, the transmitter 24 further comprises a transceiver for transmitting and receiving wireless signals, and further comprises an antenna filter for filtering radio interference. Also, the electrode patch 10 may include a light source 38, preferably a light-emitting diode, connected to the circuit board 16 to provide a visual indication of electrode patch activation. As a power source 14, the electrode patch 10 comprises a relatively flat, compact disposable battery.

Another embodiment of the invention includes an apparatus for wireless monitoring of at least one electrical signal from a patient's body. The apparatus includes the above-described disposable electrode patch 10, and a monitoring unit 40 comprising a power source 14, a transceiver in wireless communication with at least the electrode patch, a global positioning receiver, a processor 22 programmed at least to control the apparatus and to process signals received, at least one communication port 44 for external communications, and a display 46 connected to the processor 22 to visually display information from signals processed thereby. The monitoring unit 40 may further comprise an activation switch 48 for manually activating the apparatus. Generally, the monitoring unit 40 is sized so as to be portable by a patient wearing the electrode patch 10. In addition, the monitoring unit 40 may be disposed with a plurality of light sources 38, preferably light-emitting diodes, connected to function as visual indicators of apparatus status. To increase its utility, the monitoring unit 40 comprises a plurality of communication ports 44, wherein at least one communication port comprises an RS-232 port, and one communication port is responsive to infrared light.

Among other features of the invention, it should be recognized that the monitoring unit power source 14 is best a rechargeable power source such as a lithium ion battery, or similar. The invention, therefore, also includes a battery charger for the monitoring unit 40, which operates in a known fashion. Additionally, the monitoring unit 40 includes a speaker 50 connected to provide an audible signal responsive to apparatus status, and at least one scroll switch 52 connected to allow a patient to scroll through information appearing on the display 46. Most advantageously, the monitoring unit 40 is remotely programmable from a base station processor communicating therewith through at least one individual communication port of the plurality of communication ports.

An alternate embodiment of the disposable electrode patch 10 is shown in FIG. 5. In this configuration the disposable electrode patch 10 comprises a relatively thin and flexible-sealed housing 12 externally disposed with an adhesive effective for releasably adhering the patch to the patient, having an electrode docking port 54 positioned on an undersurface of the housing for therein engaging an electrode 18, and having a plurality of manually actuated stops adjacent the electrode docking port 54 for releasably securing an electrode therein engaged. Additional features of this alternate embodiment of the electrode patch 10 are as previously described. An electrode 18 releasably engaged in the electrode docking port 54 is part of the invention, so as to detect and communicate through the circuit board 16 the at least one electrical signal when the patch 10 is properly adhered to the patient's body. Other aspects of this embodiment include a converter 20 positioned in the housing 12 connected through the circuit board 16 to the electrode 18 for converting the detected electrical signal from the patient's body to a digital signal; a processor 22 having a clock and positioned in the housing connected through the circuit board 16 to the converter 20 for processing the digital signal responsive to time; a transmitter 24 having a relatively flexible antenna 26 and positioned in the housing connected to the processor 22 through the circuit board 16 for transmitting the processed digital signal as a wireless signal; and a light source 38 connected to provide a visual signal indicative of functional status of the electrode patch 10.

It should be understood that this alternate embodiment of the electrode patch 10 forms part of the invention in combination with a monitoring unit 40 comprising a power source 14, a transceiver in wireless communication with at least the electrode patch, a global positioning receiver, a processor 22 programmed to control the apparatus and to process signals received, at least one communication port 44 for external communications, and a display 46 connected to the processor 22 for visually displaying information from signals processed thereby.

A further aspect of the present invention includes a patient kit 58 for use by a patient requiring medical monitoring. The kit 58 includes a carrying case 60 disposed with interior cushioning material having a plurality of cavities therein for containing kit components, which are: a packet containing a plurality of the disposable electrode patches, a monitoring unit 40, a charger for the rechargeable power source, and an instructional video recording containing instructions for the patient on proper use of kit components.

To expand the utility of the invention, a system is provided for monitoring a plurality of patients. In the system, each of a plurality of patients wears the disposable electrode patch 10 and a monitoring unit 40. A base station processor comprising a transceiver is in wireless communication with each individual monitoring unit 40 worn by the plurality of patients so as to receive therefrom the signals processed. A display 46 connected to the base station processor displays information contained in the received signals, including patient location information received from the global positioning system 42 receiver.

Those skilled in the art will appreciate several aspects of the invention, for example, that the various electronic components should be chosen for minimum power consumption, and that the transmitters and/or transceivers may operate in the common industrial/scientific/medical range of the wireless spectrum, such as from 900-960 MHz, or others. Also, that the wireless signals may be in standard formats such as code division multiple access (CDMA), time division multiple access (TDMA), global system for mobile communications (GSM), and AMPS/ANALOG. Typical gels for use in the electrodes include the well known HydraGel and SolidGel, both of which are trademarks for proprietary compositions of electrically conductive gels. A useful power source for use in the disposable electrode patch 10 is a Panasonic Br3032 battery, or any other similar battery with about 2500 hours of capacity. Preferred batteries are replaceable, although these would not necessarily be employed in the disposable electrode patch 10. The relatively flexible circuit board 16 may be manufactured of phenolic, acetate, and/or Mylar. It should also be apparent to the skilled that this invention is equally applicable in veterinary medicine as it is in human medicine. Additionally, the advantages of the patient kit 58 herein described should be recognized by the skilled as providing great, heretofore unavailable convenience for both patients and physicians.

Figure 4A:
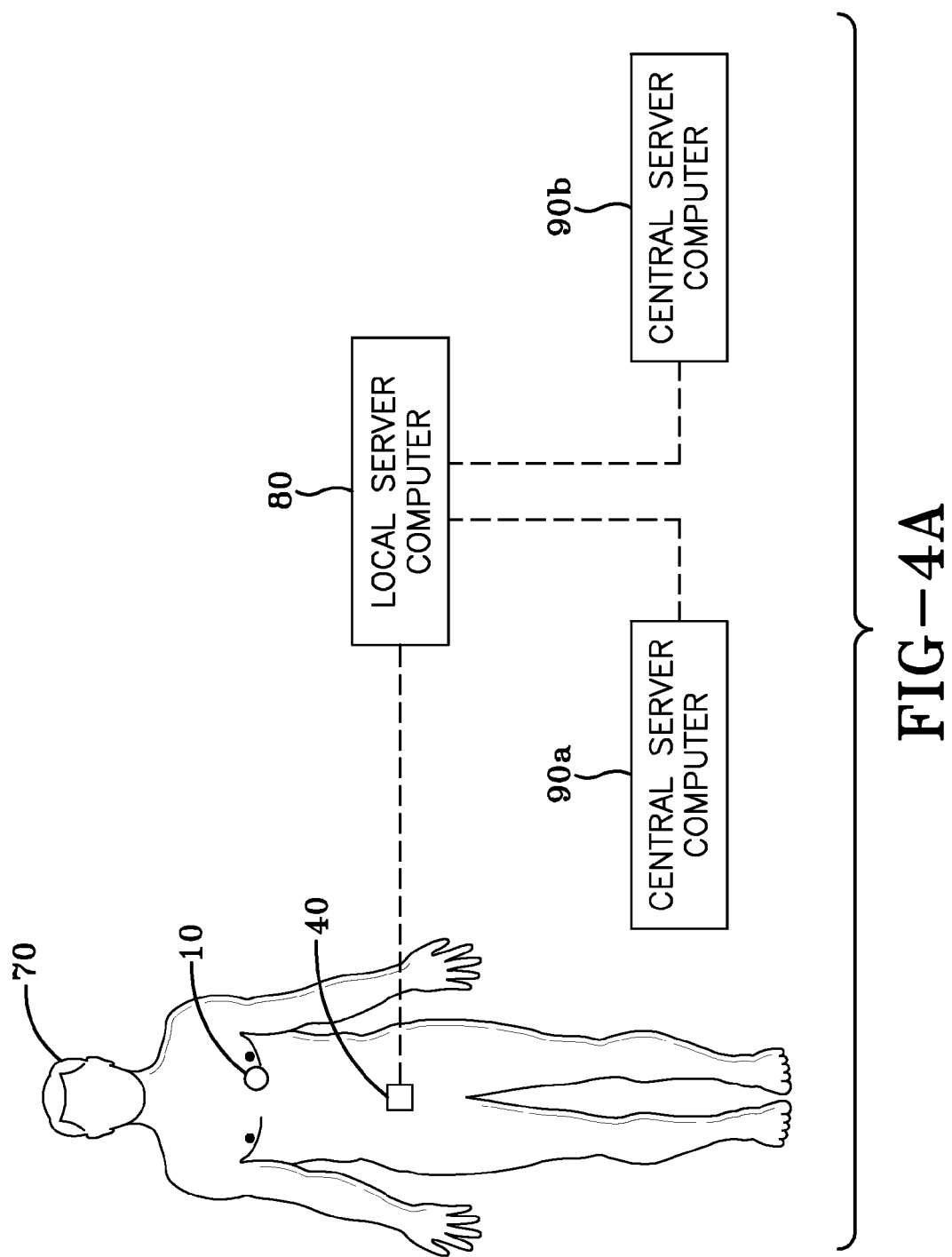
FIG. 4A is a schematic representation of the components of the apparatus attached to a person and in communication with remote components of the apparatus.
Figure 6:
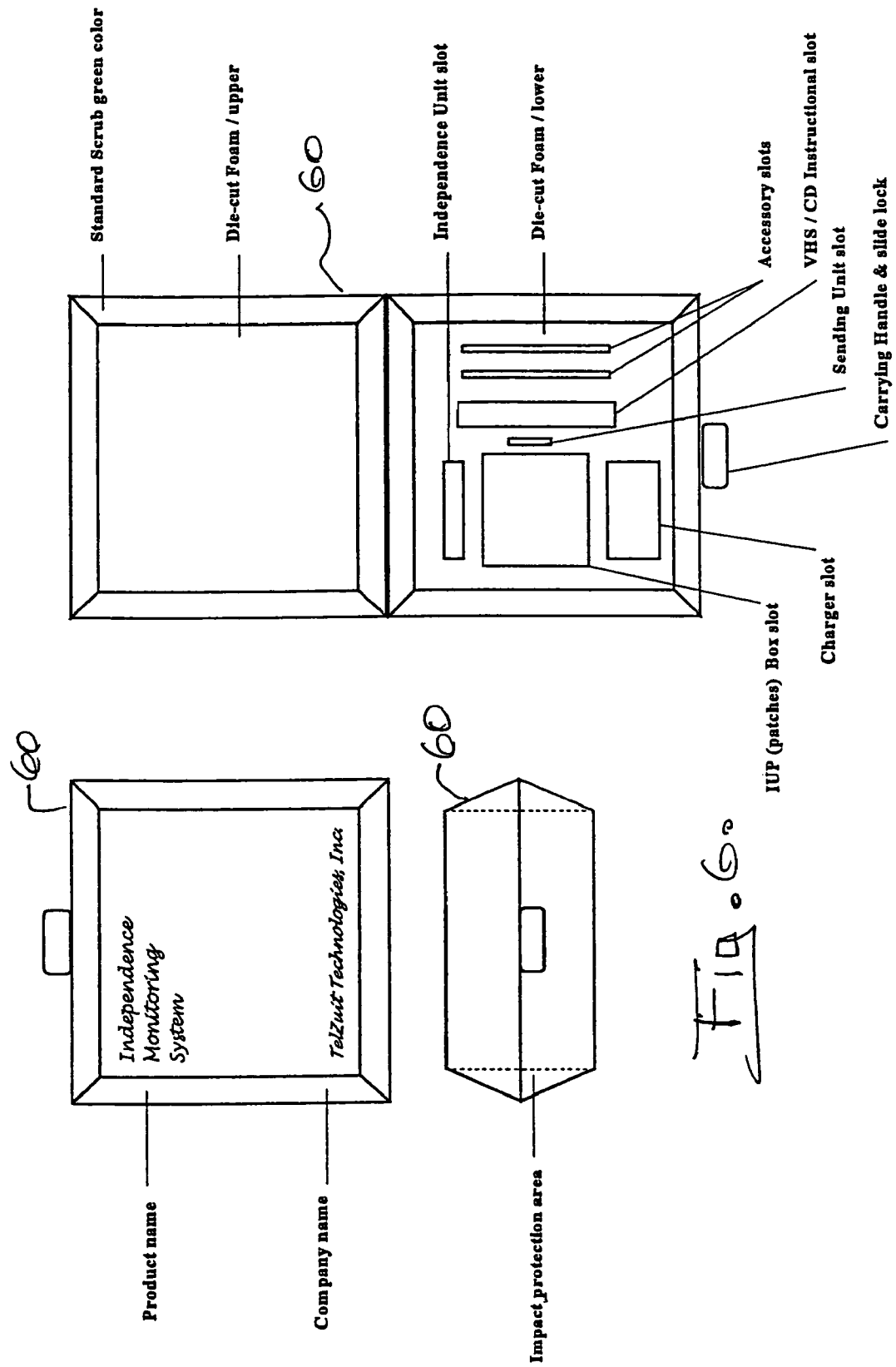
FIG. 6 illustrates the carrying case for the patient kit embodiment of the invention.

With reference to FIG. 4A, a method aspect of the present invention includes a process for transmitting the medical monitoring data, also referred to herein as biometric data or biometric information, by short range radio frequency from the electrode patch 10 adhered to the skin of a patient 70 to the monitoring unit 40 which is portable by the patient. The monitoring unit 40, in turn, transmits the data by wireless communication, preferably via a cellular telephone system, to a local server computer 80. The local server computer then transmits the data to a central server computer 90a, and for data safety preferably to two geographically separated central server computers 90a, 90b which are mirror images of each other. One of these central server computers will generally act as the primary server, and the other will remain as a mirror image backup. Medical data archived in the primary central server will be accessible through security controlled access via the Internet. Internet access may be accomplished through a portable computer or a desktop computer or other digital device such as a personal digital assistant (PDA), however, any such computer or device used for accessing the system must be capable of reading a user's fingerprint (preferably a thumb print) so that a registered user of the system may be identified and cleared for access by identification of his/her fingerprint.

The data is preferably accessed via the Internet by means of a separate Virtual Private Network (VPN), which will have access to a "download specific" database. "Download specific" means that only the biometric data of patients whose physician elects to access data via the VPN will be downloaded to this Internet accessible database.

In use, the biometric data and a unique identifier is transmitted short range from the electrode patch 10 to the monitoring unit 40 transceiver. The identifier is then encrypted and along with the biometric data they are transmitted first via cellular network then via a private intranet that uses frame relay, satellite and dedicated ISDN to transmit the data to two geographically separated collection points. Servers at the collection points will allow communication with the transceiver only if the signal includes a prearranged code that must match both the short range transmitter's own unique identifier and the transceiver's unique identifier. The communication will be accepted, and biometric data will be allowed into the network only after this "handshake" occurs.

Once biometric data is received at the collection points, each collection point will immediately duplicate the data and send it preferably over three separate communication lines: wirelessly via satellite, by a dedicated frame relay circuit, and by a dedicated ISDN circuit to two national data centers. These data centers are separated geographically, and run in tandem. Each collection point and each data center preferably contains redundant systems as well as redundant power supplies and redundant emergency generators.

Any measurable or imaged data of the human body that is transmitted into this network is then archived or stored for as long as required by applicable regulations. These data are then made available via the described intranet almost immediately, preferably within minutes. It should be understood that these data are not medical records; but biometric data or images that support the doctor's diagnosis.

Each hardware component that communicates with the system must have both the computer processor 22's unique identifier and the network interface card's unique identifier registered with the network. Additionally, authorized individuals must also be registered with the network via registry of their fingerprint or thumb print prior to authorized access to the databases. The network will only allow access if the required fingerprint or thumb print is matched with both the computer's processor 22 and the network interface card's unique identifier as a set. Specific network configuration parameters will be implemented for both national and international use of the described system.

With reference to drawing FIG. 1 it can be seen that the housing of the disposable electrode patches 10 of this embodiment of present invention has a single continuous surface with a pair of end portions and a center portion disposed between the end portions, each of the end portions having a width that is greater than a width of the center portion. The electrodes 18 are positioned in only the end portions of said housing and are spaced apart.

Accordingly, in the drawings and specification, there have been disclosed typical preferred embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made in the spirit and scope of the invention as described in the foregoing specification and as defined in the appended claims.

That which is claimed:

1. An apparatus for wireless monitoring of at least one electrical signal from a patient's skin, said apparatus comprising in combination a disposable electrode patch and a monitoring unit:

the disposable electrode patch having a relatively thin and flexible sealed housing having an adhesive surface effective for releasably adhering said electrode patch to the patient's skin, said housing having a single continuous surface with a pair of end portions and a center portion disposed between the end portions, each of the end portions having a width that is greater than a width of the center portion, a power source comprising a disposable battery positioned in the housing for providing power, the housing further containing a printed circuit board operatively connected to the power source for distributing power, a plurality of electrodes operably connected with said circuit board and positioned only in the end portions of said housing and are spaced apart so as to detect the electrical signal when the patch is properly adhered to the patient's skin, one of the electrodes being a ground electrode for grounding the electrode patch to the patient, a converter connected with said plurality of electrodes for receiving a plurality of detected electrical signals and for converting the plurality of detected electrical signals to a single digital signal, a processor having a clock and connected with said converter for processing the digital signal responsive to time, a transceiver for transmitting and receiving wireless signals, the transceiver connected with said processor for transmitting a processed digital signal via an antenna positioned in the housing as a wireless signal by short range radio frequency to the monitoring unit; and the monitoring unit being reusable and portable by the patient, the monitoring unit comprising a transceiver effective in wireless communication with said electrode patch for receiving the wireless signal transmitted by the electrode patch and then transmitting the processed digital signal via a cellular telephone system to a computer, the monitoring unit further comprising at least one communication port for external communications and the monitoring unit is remotely programmable from a base station processor communicating therewith through at least one communication port.

2. The apparatus of claim 1, wherein said monitoring unit further comprises an activation switch for manually activating said apparatus.

3. The apparatus of claim 1, wherein said monitoring unit further comprises a plurality of light sources connected to function as visual indicators of apparatus status.

4. The apparatus of claim 1, wherein at least one communication port comprises an RS-232 port.

5. The apparatus of claim 1, wherein at least one communication port is responsive to infrared light.

6. The apparatus of claim 1, wherein said monitoring unit further comprises a power source that is rechargeable.

7. The apparatus of claim 6, wherein said monitoring unit power source is a rechargeable battery and further comprising a battery charger therefore.

8. The apparatus of claim 1, wherein said monitoring unit further comprises a speaker connected to provide an audible signal responsive to apparatus status.

9. The apparatus of claim 1, wherein said monitoring unit further comprises at least one scroll switch connected to allow a patient to scroll through information appearing on a display.

10. The apparatus of claim 1, wherein said monitoring unit further comprises a global positioning receiver.

11. The apparatus of claim 1, wherein said monitoring unit further comprises a processor programmed to control the apparatus and to process signals received via said transceiver.

12. The apparatus of claim 11, wherein said monitoring unit further comprises a display connected to said processor to visually display information from signals processed thereby.

* * * * *